United States Patent
Brown

[11] Patent Number: 5,761,746
[45] Date of Patent: Jun. 9, 1998

[54] WATERPROOF SLEEVE

[76] Inventor: Ella K. Brown, 28 Telegraph Hill Rd., Holmdel, N.J. 07733

[21] Appl. No.: 852,397

[22] Filed: May 7, 1997

[51] Int. Cl.$^6$ .................................................. A41B 11/00
[52] U.S. Cl. ..................... 2/243.1; 2/239; 2/16; 2/59; 2/61; 36/110; 602/3; 128/856
[58] Field of Search ................... 2/243.1, 46, 59, 2/61, 68, 69, 158, 159, 161.6, 161.7, 167, 168, 239, 174, 200.2; 36/87, 102, 110, 7.1 R, 7.4, 7.3, 7.6, 8.1, 4; 602/3; 128/856

[56] References Cited

U.S. PATENT DOCUMENTS

| | | | |
|---|---|---|---|
| 1,074,595 | 10/1913 | Aumont | 2/239 |
| 2,244,871 | 6/1941 | Guinzburg | 2/59 |
| 2,326,422 | 8/1943 | Weisberger | 2/59 |
| 2,582,648 | 1/1952 | Mowbray | 2/239 |
| 3,329,143 | 7/1967 | Gordon | 2/239 |
| 3,657,741 | 4/1972 | Blanco | 2/59 |
| 4,036,220 | 7/1977 | Bellasalma | 2/59 |
| 4,069,600 | 1/1978 | Wise | 2/239 |
| 4,986,265 | 1/1991 | Caponi | 602/3 |
| 5,063,919 | 11/1991 | Silverberg | 2/59 |
| 5,575,014 | 11/1996 | Kane et al. | 2/239 |
| 5,592,953 | 1/1997 | Delao | 602/3 |
| 5,682,617 | 11/1997 | Tumas | 2/239 |

*Primary Examiner*—Gloria M. Hale
*Attorney, Agent, or Firm*—Charles I. Brodsky

[57] ABSTRACT

A sleeve for the keeping dry of arms, legs, hands or feet while washing, bathing and/or showering of upper and lower section, with the lower section being composed of a waterproof material stretchable in both longitudinal and latitudinal planes, and with the upper section being composed of a waterproof material exhibiting a substantial adherence characteristic, and including an elastic band for sealing-off the upper section when in use.

6 Claims, 1 Drawing Sheet

WATERPROOF SLEEVE

FIELD OF THE INVENTION

This invention relates to the healing of fractured, injured, burned and/or diseased body parts and, more particularly, to a sleeve for the keeping dry of arms, legs, hands or feet while washing, bathing and/or showering.

BACKGROUND OF THE INVENTION

As is well known and understood, fractured, injured, burned and/or diseased body parts are almost always bandaged, casted or wrapped after treatment, and for various purposes. Most obviously, one purpose is to keep the treated area covered and protected against further damage. In similar fashion, these bandages, casts and/or wrappings are employed to keep in place, uncontaminated, topical medications, salves, ointments, and treatments in place, continuing to give the relief intended. While these bandages and wrappings perform adequately well when they are kept dry, their benefits deteriorate quickly if they somehow become wet—as may occasionally happen if being worn out of doors on a rainy or snowy day—but as always happens if they become wet during washing, bathing and/or showering. In those instances, the ability of the bandage or wrap to continue to adhere to the skin diminishes quickly, leading to the possibility of their then becoming easier to accidentally dislodge and loosen, and to thereby diminish the protection that they were intended to afford. But even if that were not the situation, the wetting of the bandage, cast or wrapping allows the introduction of water, soap, or other astringents into the wound area, for example, to adversely offset the benefits that the applied topical medication were intended to produce.

As is well known, the procedure most often prescribed by physicians to prevent this is for the patient to put on a plastic leaf bag, or garbage bag, on the area to be protected, close it off with a rubber band around it, and then put that combination inside a second similar type plastic bag, closing that off in a similar fashion. Whereas such arrangement has proved quite effective over the years, it will be apparent that it is not only cumbersome to put on, but quite awkward in use. Clearly, one further disadvantage of this type of arrangement is that a far greater amount of material is utilized in protecting the area than is actually necessary—for example, where only a hand is to be kept dry, and it is inserted into a garbage-can size bag—let alone requiring a user to be able to find a rubber band or tape large enough to encircle the area (in this case a forearm), while holding the plastic bag firmly in place.

OBJECTS OF THE INVENTION

It is an object of the present invention, therefore, to provide a new and improved arrangement for the keeping dry of arms, legs, hands or feet while washing, bathing and/or showering.

It is an object of the present invention, also, to provide such an arrangement available in a variety of sizes, for both adults and children, and for the protection of different parts of the body.

It is another object of the invention to provide such an arrangement which eliminates the need for leaf or garbage bags, and for rubber bands or tapes to tie them off.

It is an additional object of the invention to provide this arrangement which can be reused more easily than those previously employed with the leaf and garbage bag types of constructions, which typically are discarded after one, two or three uses.

It is yet another object of the invention to provide such a new and improved arrangement which can even be employed in keeping dry fractured, injured, burned or diseased parts of animals, treated by veterinarians, whose legs, paws, and other body areas are intended to be kept dry as well, as part of a recovery procedure.

It is yet a further object of the present invention to provide such an arrangement as a self-contained unit, without any need for separate closures as rubber bands, tape, or ties, for example, for closing the arrangement, or for holding it in place.

SUMMARY OF THE INVENTION

As will be seen from the description that follows, the present invention comprises a sleeve of upper and lower sections, with the lower section being composed of a waterproof material stretchable in both longitudinal and latitudinal planes, with the upper section being composed of a waterproof material exhibiting a substantial adherent characteristic, and including means for sealing of the upper section when in use. As will be seen, in a preferred embodiment of the invention, both the upper and lower sections are of a synthetic plastic composition, and with the lower section being of a length substantially greater than the length of the upper section. To close off the upper section in protecting the arms, legs, hands or feet while washing, bathing and/or showering, an elastic band may be employed at a top portion of the upper section, where it encircles the upper section. In a preferred embodiment of this arrangement, as will be described, the upper section comprises a wide band of stretchable waterproof material.

As will be appreciated, by employing an upper section of a substantial adherence characteristic, that upper section can then be compressed into position about the body part, in assisting to hold the sleeve in place. By employing the upper and lower sections of waterproof material, the sleeve can serve for keeping such body parts dry. By employing a sleeve of upper and lower sections, each of which is stretchable, the adherence of the sleeve to the body part being protected is enhanced, and affords a type of form-fitting shape to the sleeve, reducing its degree of cumbersomeness and awkwardness. By having its lower section stretchable in both longitudinal and latitudinal planes, the sleeve will be seen to afford its protection whether it be intended for use in keeping dry arms, legs, hands or feet, without having to design a plethora of shapes conforming to the body part to be protected. By employing an elastic band at a top portion of the upper section to seal it off when in use, a sleeve results which does not need any separate rubber band, tape or tie to hold it in position. As will be appreciated by those skilled in the art, all that becomes necessary is to then have this sleeve of the invention in sizes small, medium or large, for example, to conform for use with small children, medium-sized adults, or large adults. In this respect, it will be appreciated that the "small", "medium" and "large" sizes can be with respect either to the "width" of the waterproof sleeve intended, or to the "length" of the sleeve—again, for short persons, medium-height individuals, and tall people, as well.

BRIEF DESCRIPTION OF THE DRAWING

These and other features of the invention will be more clearly understood from a consideration of the sole FIGURE of the Drawing which pictorially illustrates a waterproof sleeve constructed in accordance with a preferred embodiment of the invention.

DETAILED DESCRIPTION OF THE DRAWING

Figure 1:
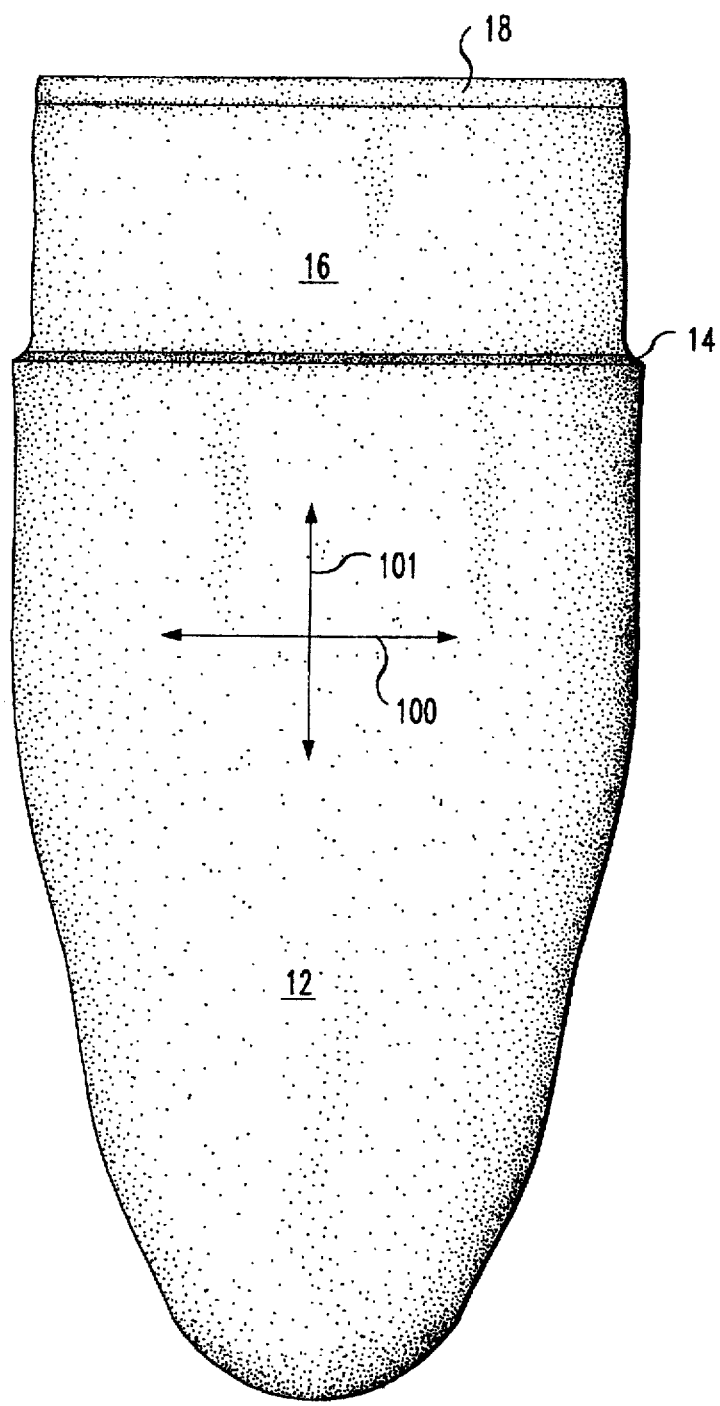

The waterproof sleeve 10 of the Drawing incorporates a lower section 12, composed of a waterproof material stretchable in both longitudinal and latitudinal planes, as indicated at 100, 101 and closed at its bottom end. Joined at the seam line 14 is an upper section 16 of the sleeve 10, also composed of a waterproof, stretchable material open at its top end. Such upper and lower sections 16, 12 are of a synthetic plastic composition, but with the upper section 16 exhibiting a substantial adherence characteristic so that when it is brought in contact with the body, or with a bandage, wrapping or cast, essentially clings to it in similar manner as when a rubber glove is put on and clings to the hand or forearm, or like the clinging associated with Latex or Saran Wrap material. While such lower section 12 could be of synthetic plastic composition to "form-fit" over the bandage, wrapping or cast intended to be kept dry, that is not a necessity in accordance with the invention, as it is intended that the lower section 12 be stretchable in the planes 100, 101 so as to accept the different size bandages, wrappings and/or casts to be encountered.

The upper section 16, on the other hand, essentially comprises a wide band of the stretchable synthetic plastic waterproof material, whose adherence characteristic enables it to adhere to the skin, or to the bandage, wrapping or cast which is being protected. To such end, an elastic band 18 is further provided, at a top portion of the upper section 16, where it encircles that upper section. In such manner, the adherence characteristic of the upper section 16 conforms it to the configuration around which it goes, while the elastic band 18 snugly fits the upper section in position around the limb, yet without being so tight as to cut off circulation. As will be appreciated, in this respect, the combination of the elastic band 18, the stretchable nature of its waterproof band material 16 and the seam 14 cooperate in preventing any inflow of water, soap or astringent into the lower section 12, within which the arm, leg, hand or foot is first inserted prior to washing, bathing and/or showering, or into which the body part of the dog, cat or other animal to be protected is first inserted in similar fashion. Such elastic band 18, as being part of the upper section 16 of the sleeve thus will be seen to obviate the need for a separate rubber band, tape, or tie as characterized prior art arrangements of this type, enabling the sleeve of the invention to be a unified construction.

Of course, depending upon the ultimate user of the sleeve, the dimensions selected for the upper and lower sections 16, 12, respectively, can be tailored in size for both small, medium and large employments, depending upon the needs of the situation.

While there have been described what are considered to be preferred embodiments of the invention, it will be readily appreciated by those skilled in the art that modifications can be made without departing from the scope of the teachings herein, of employing a waterproof sleeve with a self-sealing closure, in fitting over any type and size of body part to be kept dry and to prevent water, soap and/or astringent from reaching that area when washing, bathing and/or showering. For at least such reason, therefore, resort should be had to the claims appended hereto for a true understanding of the scope of the invention.

I claim:

1. A sleeve for the keeping dry of arms, legs, hands or feet while washing, bathing and/or showering, comprising a lower section composed of a waterproof material stretchable in both longitudinal and latitudinal planes and closed at a bottom end, an upper section having an open top end composed of a waterproof material exhibiting a substantial adherence characteristic to cling to skin, bandages, wrappings and castings, a seam securing said upper and lower sections together, and means at said top end of said upper section for sealing-off said top end of said upper section when in use with said upper and lower sections, with said seam, and with said means cooperating to provide a one-piece, self-sealing sleeve protection against water intrusion.

2. The sleeve of claim 1 wherein said lower section is of a first length, wherein said upper section is of a second length, and wherein said lower section is of a length substantially greater than the length of said upper section.

3. The sleeve of claim 2 wherein said sealing means includes an elastic band at said top portion of said upper section, and encircling said upper section thereat.

4. The sleeve of claim 2 wherein said upper section comprises a wide band of stretchable waterproof material.

5. The sleeve of claim 2 wherein said upper and lower sections are of a synthetic plastic composition.

6. The sleeve of claim 2 wherein said upper section is of a synthetic plastic composition.

* * * * *